US011517329B2

(12) United States Patent
Koogle, Jr. et al.

(10) Patent No.: US 11,517,329 B2
(45) Date of Patent: Dec. 6, 2022

(54) EXPANDABLE REAMER

(71) Applicant: ARTHREX, INC., Naples, FL (US)

(72) Inventors: David C. Koogle, Jr., Bonita Springs, FL (US); Zachary A. Ingwer, Boca Raton, FL (US); Michael E. Eggert, Naples, FL (US)

(73) Assignee: ARTHREX, INC., Naples, FL (US)

( * ) Notice: Subject to any disclaimer, the term of this patent is extended or adjusted under 35 U.S.C. 154(b) by 399 days.

(21) Appl. No.: 16/686,555

(22) Filed: Nov. 18, 2019

(65) Prior Publication Data

US 2020/0078028 A1 Mar. 12, 2020

Related U.S. Application Data

(62) Division of application No. 14/091,902, filed on Nov. 27, 2013, now Pat. No. 10,499,932.

(60) Provisional application No. 61/774,787, filed on Mar. 8, 2013.

(51) Int. Cl.
*A61B 17/16* (2006.01)
*A61B 17/88* (2006.01)
*A61B 17/32* (2006.01)

(52) U.S. Cl.
CPC ......... *A61B 17/1668* (2013.01); *A61B 17/16* (2013.01); *A61B 17/1617* (2013.01); *A61B 17/8858* (2013.01); *A61B 17/32002* (2013.01); *A61B 17/320016* (2013.01)

(58) Field of Classification Search
CPC . A61B 17/16; A61B 17/1615; A61B 17/1617; A61B 17/1637; A61B 17/1633; A61B 17/1675; A61B 17/1664–1671; A61B 17/1684; A61B 17/8847; A61B 17/885; A61B 17/8852; A61B 17/8858; A61B 2017/1602; B26B 1/08
USPC .......................................... 30/153, 155–161
See application file for complete search history.

(56) References Cited

U.S. PATENT DOCUMENTS

| 1,410,080 | A | 3/1922 | Schwahlen |
| 3,008,360 | A | 11/1961 | Winberry, Jr. |
| 3,195,378 | A | 7/1965 | Cogsdill |
| 4,475,852 | A | 10/1984 | Koppelmann |
| 4,992,010 | A | 2/1991 | Fischer |
| 5,591,170 | A | 1/1997 | Spieack et al. |
| 5,928,239 | A * | 7/1999 | Mirza ............ A61B 17/320725 606/167 |
| 2001/0034526 | A1 | 10/2001 | Kuslich et al. |
| 2004/0092933 | A1 * | 5/2004 | Shaolian ............ A61B 17/1675 606/279 |

(Continued)

FOREIGN PATENT DOCUMENTS

| DE | 23 49 998 | 4/1975 |
| EP | 1714618 A2 | 10/2006 |

OTHER PUBLICATIONS

"Advanced Core Decompression System, X-Ream, Pro-Stim, Surgical Technique," Wright Medical Technology, Inc., pp. 1-12.

(Continued)

*Primary Examiner* — Amy R Sipp
(74) *Attorney, Agent, or Firm* — Carlson, Gaskey & Olds, P.C.

(57) ABSTRACT

A surgical device may include a tube and a cutting blade movable between a first position in which the cutting blade is concealed inside the tube and a second position in which the cutting blade is exposed through a sidewall of the tube.

15 Claims, 7 Drawing Sheets

(56) References Cited

U.S. PATENT DOCUMENTS

| | | |
|---|---|---|
| 2005/0277971 A1 * | 12/2005 | Melkent ............ A61B 17/1671 606/180 |
| 2006/0057184 A1 | 3/2006 | Nycz et al. |
| 2006/0241629 A1 | 10/2006 | Krebs et al. |
| 2008/0114364 A1 | 5/2008 | Goidin et al. |
| 2009/0275950 A1 | 11/2009 | Sterrett et al. |
| 2010/0168750 A1 | 7/2010 | Sherman |
| 2011/0130760 A1 | 6/2011 | Anderson et al. |
| 2011/0238074 A1 | 9/2011 | Ek |
| 2012/0004594 A1 | 1/2012 | Schulz et al. |
| 2012/0271357 A1 | 10/2012 | Arthur et al. |

OTHER PUBLICATIONS

Extended European Search Report for Application No. 14 157 959.9 dated May 30, 2014.
Extended European Search Report for Application No. 17 181 267.0 dated Jan. 23, 2018.

* cited by examiner

EXPANDABLE REAMER

CROSS-REFERENCE TO RELATED APPLICATION

This is a divisional of U.S. patent application Ser. No. 14/091,902, filed on Nov. 27, 2013, which claims priority to U.S. Provisional Application No. 61/774,787, which was filed on Mar. 8, 2013, the entire disclosures of which are hereby incorporated by reference.

BACKGROUND

This disclosure relates to an orthopedic surgical device, and more particularly to an expandable reamer that can be introduced into a bone tunnel to remove areas of diseased bone.

Diseased areas of bone may need removed from patients suffering from bone degeneration. For example, treatment of Avascular Necrosis (AVN) of the hip is often performed on patients that may otherwise face prosthetic joint arthroplasty, which can be a relatively invasive procedure. Core decompression procedures have been used to remove areas of diseased bone. However, efforts have continued to develop improved procedures for removing areas of diseased bone.

SUMMARY

A surgical device according to an exemplary aspect of the present disclosure includes, among other things, a tube and a cutting blade movable between a first position in which the cutting blade is concealed inside the tube and a second position in which the cutting blade is exposed through a sidewall of the tube.

In a further non-limiting embodiment of the foregoing surgical device, a shaft is surrounded by the tube.

In a further non-limiting embodiment of either of the foregoing surgical devices, one of the tube and the shaft is movable relative to the other of the tube and the shaft.

In a further non-limiting embodiment of any of the foregoing surgical devices, a plurality of cutting blades are moveable to a cutting position radially outward of the tube.

In a further non-limiting embodiment of any of the foregoing surgical devices, the tube includes a window disposed through the sidewall and the cutting blade is incrementally advanced though the window to expose the cutting blade.

In a further non-limiting embodiment of any of the foregoing surgical devices, a clutch assembly is configured to move the cutting blade between the first position and the second position.

In a further non-limiting embodiment of any of the foregoing surgical devices, the clutch assembly includes a threaded hub and a clutch hub disengageable from the threaded hub.

In a further non-limiting embodiment of any of the foregoing surgical devices, the tube includes a deflection pin configured to deflect the cutting blade radially outward of the tube.

In a further non-limiting embodiment of any of the foregoing surgical devices, the tube is connected to a handle.

In a further non-limiting embodiment of any of the foregoing surgical devices, the cutting blade includes nitinol wires having a shape memory.

In a further non-limiting embodiment of any of the foregoing surgical devices, an actuator is configured to move the cutting blade between the first position and the second position.

An expandable reamer according to another exemplary aspect of the present disclosure includes, among other things, a tube and at least one cutting blade configured to incrementally advance to a cutting position radially outward from the tube to create a socket in bone.

In a further non-limiting embodiment of the foregoing expandable reamer, a shaft has a concentric relationship with the tube.

In a further non-limiting embodiment of either of the foregoing expandable reamers, the cutting blade is hinged to the shaft.

In a further non-limiting embodiment of any of the foregoing expandable reamers, the tube includes a guide pin received by a slot of the shaft to guide the tube as it moves relative to the shaft.

A method for removing diseased bone, according to another exemplary aspect of the present disclosure includes, among other things, positioning a surgical device relative to diseased bone, the surgical device including at least one cutting blade that is concealed inside the surgical device during the step of positioning, and incrementally advancing the at least one cutting blade to position the at least one cutting blade into a cutting position relative to the diseased bone.

In a further non-limiting embodiment of the foregoing method, the method includes the step of rotating the surgical device to remove the diseased bone.

In a further non-limiting embodiment of either of the foregoing methods, the method includes reaming a tunnel into a bone that includes the diseased bone prior to the step of positioning.

In a further non-limiting embodiment of any of the foregoing methods, the method includes backfilling the tunnel with a biologic after the step of incrementally advancing the at least one cutting blade.

In a further non-limiting embodiment of any of the foregoing methods, the step of incrementally advancing includes axially moving a tube or shaft of the surgical device to rotationally move the at least one cutting blade to the cutting position.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Among other features, this disclosure relates to a surgical device, such as an expandable reamer, that can be introduced through a bone tunnel to remove areas of diseased bone. In one non-limiting embodiment, the expandable reamers described by this disclosure can be used to treat Avascular Necrosis (AVN) of the hip. However, this disclosure is not limited to the treatment of AVN and could extend to other treatments, such as Osteochondritis Dissecans (OCD) of the knee or any other treatment requiring the removal of diseased bone in either human or animal patients.

Figure 1A:
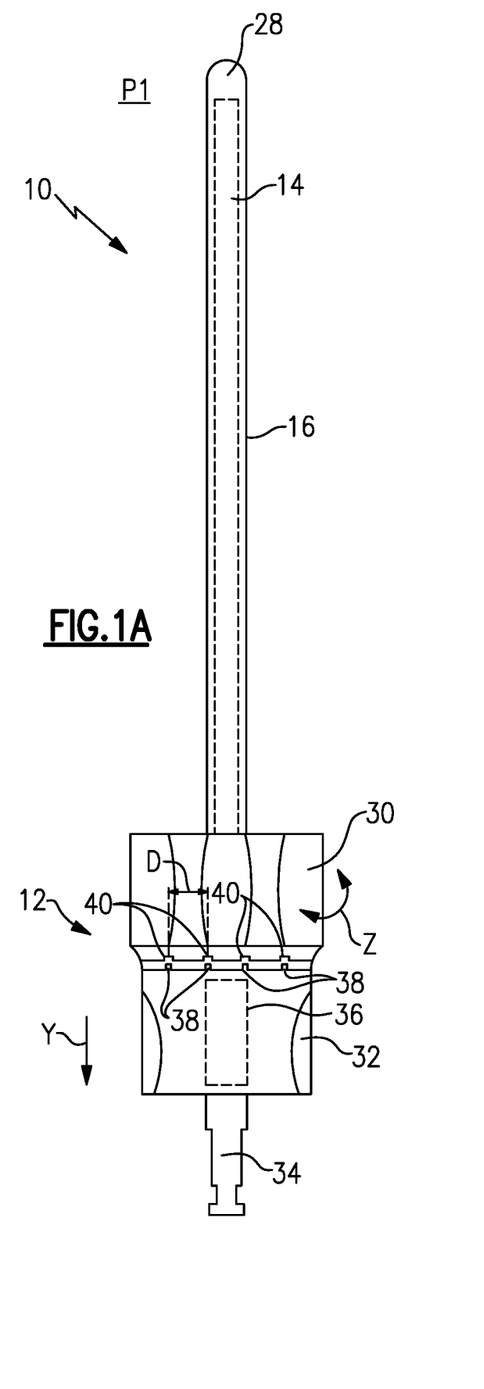
FIGS. 1A and 1B illustrate an exemplary expandable reamer.
Figure 1B:
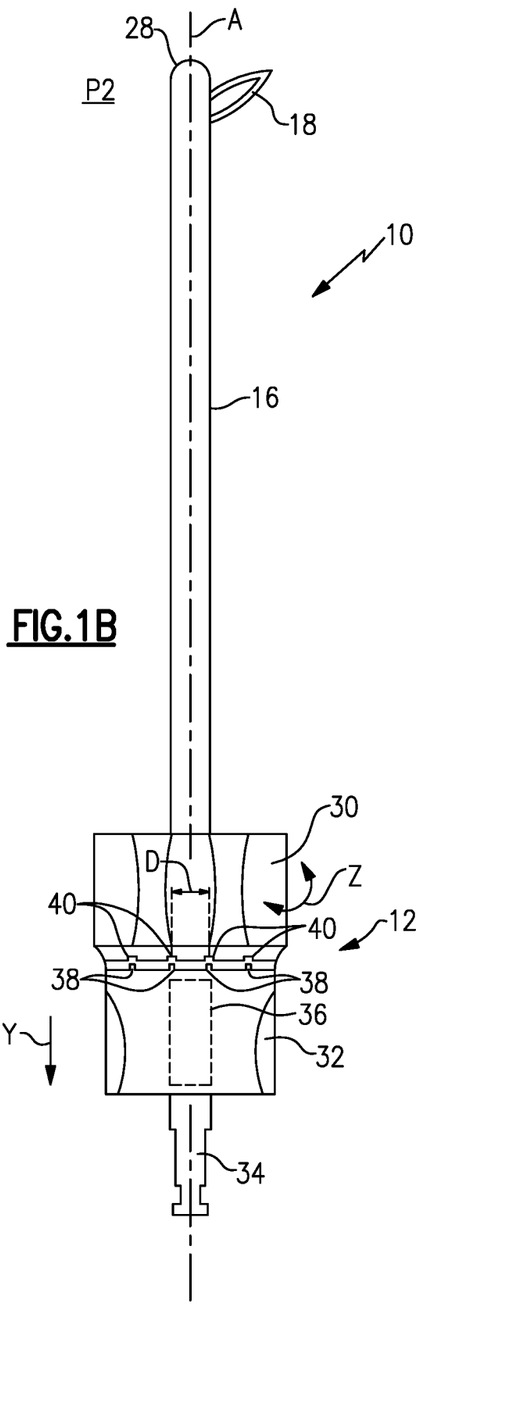
Figure 2:
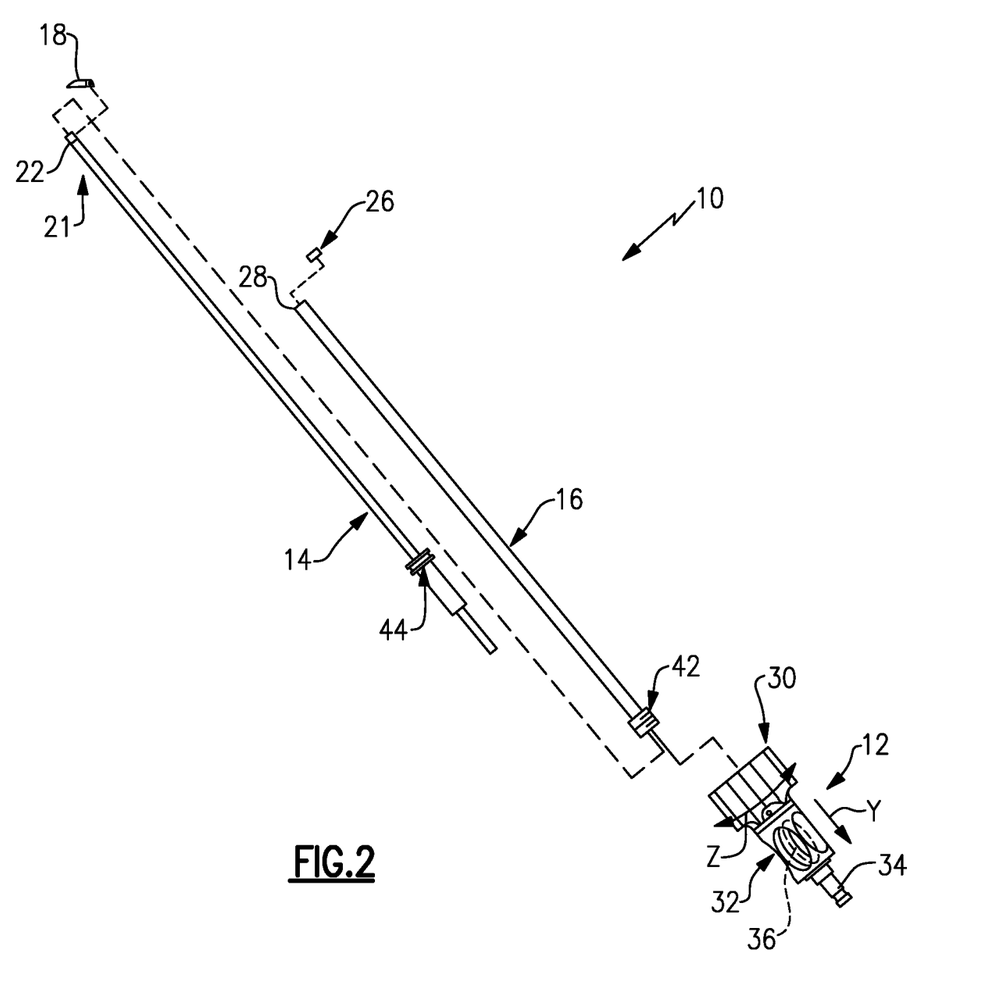
FIG. 2 illustrates an exploded view of the expandable reamer of FIGS. 1A and 1B.

FIGS. 1A, 1B and 2 illustrate an exemplary expandable reamer 10. The expandable reamer 10 is an orthopedic surgical device that may be part of a surgical instrumentation set for removing diseased bone from a patient. In one embodiment, the expandable reamer 10 includes a clutch assembly 12, an inner shaft 14 (best illustrated in FIG. 2), and an outer tube 16 that generally surrounds the inner shaft 14. For example, the inner shaft 14 and the outer tube 16 may include a concentric relationship relative to one another.

In one non-limiting embodiment, the inner shaft 14 is affixed to the clutch assembly 12 and the outer tube 16 is movable along a longitudinal axis A (see FIG. 1B) of the expandable reamer 10. An opposite configuration is also contemplated in which the outer tube 16 is affixed and the inner shaft 14 is moveable along the longitudinal axis A. Movement of either the inner shaft 14 or the outer tube 16 relative to the other of the inner shaft 14 and the outer tube 16 positions a cutting blade 18 for reaming diseased tissue, as discussed in greater detail below.

The expandable reamer may include one or more cutting blades 18. In this embodiment, a single cutting blade 18 is shown. However, multiple cutting blades could also be provided (see, e.g., the embodiment of FIGS. 10A, 10B, 11A and 11B).

Figure 3A:
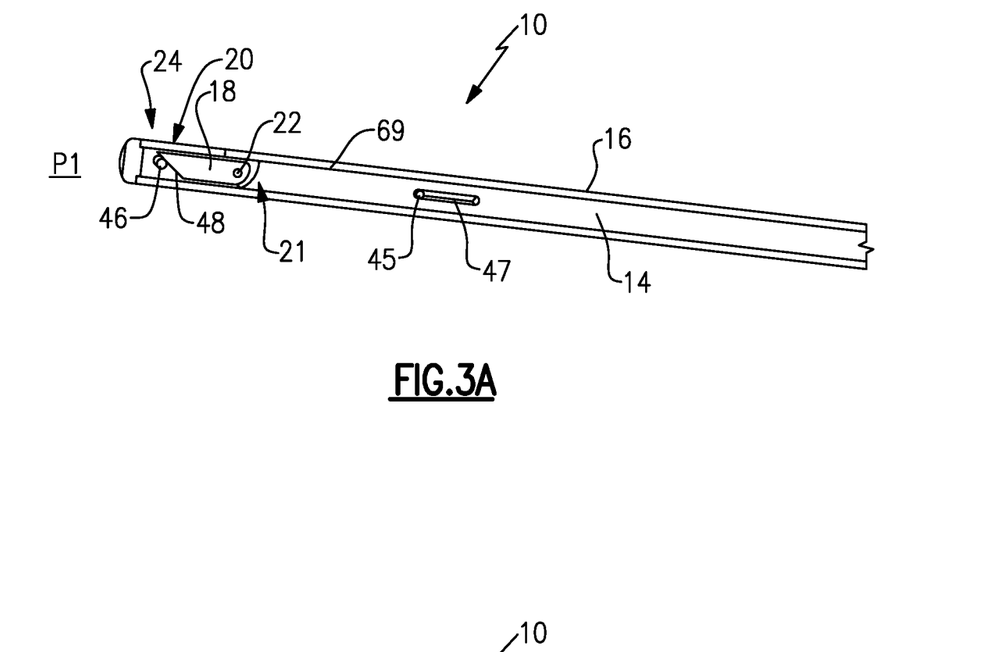
FIGS. 3A and 3B illustrate additional features of an expandable reamer.
Figure 3B:
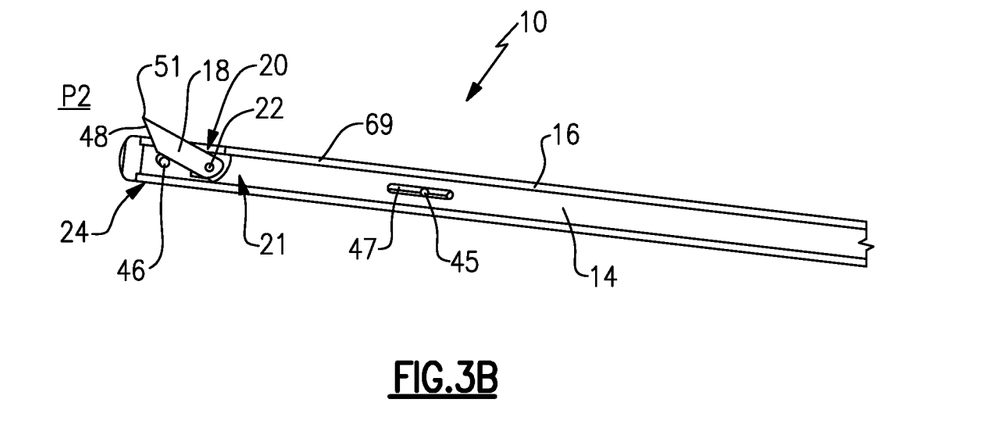

The cutting blade 18 may be attached to a distal end portion 21 of the inner shaft 14, such as with a pin 22 (i.e., the cutting blade 18 is hinged to the inner shaft 14, see FIGS. 2, 3A and 3B). In one embodiment, the cutting blade 18 may be incrementally advanced through a window 20 (best illustrated in FIGS. 3A and 3B) disposed at a distal end portion 24 of the outer tube 16 to create a retrograded socket in bone that can be filled with biologics. In one embodiment, the window 20 extends through a sidewall 69 of the outer tube 16 such that the cutting blade 18 is exposed outside of the outer tube 16 through the sidewall 69.

A cap 26 (see FIG. 2) may be welded or otherwise affixed to a distal-most portion 28 of the outer tube 16 such that the outer tube 16 includes at least one closed end. In this way, in a closed position P1 of the cutting blade 18 (see FIG. 1A), the expandable reamer 10 provides an atraumatic device that substantially reduces risk of inadvertent damage to surrounding tissue during positioning of the expandable reamer 10. The cutting blade 18 of the expandable reamer 10 may be advanced radially outward from the outer tube 16 to a cutting position P2 (see FIG. 1B) that is configured to prepare a socket in bone. In the cutting position P2, the cutting blade 18 is non-parallel to the longitudinal axis A and is exposed outside of the outer tube 16.

In one embodiment, the clutch assembly 12 of the expandable reamer 10 includes a threaded hub 30, a clutch hub 32 and a connector 34, such as a Hudson connector for connecting to powered equipment. The threaded hub 30 and the clutch hub 32 may be disengaged from one another to advance or retract the cutting blade 18. For example, the clutch hub 32 may be moved in a Y direction (e.g., away from the threaded hub 30) to overcome a biasing force of a spring 36 located within the clutch hub 32 to disengage the clutch hub 32 from the threaded hub 30. When disengaged, teeth 38 of the clutch hub 32 are removed from recesses 40 of the threaded hub 30 (or vice versa) such that the threaded hub 30 may be turned in the Z direction to either advance or retract the cutting blade 18 between the positions P1 and P2. It should be understood that the cutting blade 18 could be incrementally advanced to any position between positions P1 and P2.

A distance D between each tooth/recess 38, 40 of the threaded hub 30 and/or the clutch hub 32 may correspond to a specific radially outward advancement of the cutting blade 18. In other words, the cutting blade 18 may be incrementally advanced or retracted. In one non-limiting embodiment, the cutting blade 18 is incrementally advanceable by a distance of between 7 and 10 millimeters (0.276 to 0.394 inches). However, other advancement and retraction distances are also contemplated as within the scope of this disclosure.

In one embodiment, best illustrated in FIG. 2, the outer tube 16 includes a threaded proximal end portion 42 that is received by a corresponding threaded portion (not shown) of the threaded hub 30. The inner shaft 14 may include a connector 44 for attaching the inner shaft 14 to the threaded hub 30. In one embodiment, the threaded hub 30 is pinned to the connector 44. Turning the threaded hub 30 in the Z direction moves the threaded hub 30 relative to the threaded proximal end portion 42 in order to axially advance or retract the outer tube 16 relative to the threaded hub 30.

Referring to FIGS. 3A and 3B, axial (i.e., linear) movement of the outer tube 16 (which is caused by rotational movement of the threaded hub 30) can be converted to rotational movement of the cutting blade 18 to position the cutting blade 18 in the cutting position P2. The outer tube 16 may include a deflection pin 46 that deflects a tip 51 of the cutting blade 18 radially outwardly from the window 20. For example, a tapered edge 48 of the cutting blade 18 may contact the deflection pin 46 during linear movement of the outer tube 16 to expose the cutting blade 18. In other words, the deflection pin 46 acts as a ramp to cause the cutting blade 18 to rotate about an axis that extends through the pin 22, thereby incrementally advancing the cutting blade 18 radially outwardly from the window 20 to the cutting position P2 (see FIGS. 1B and 3B). The outer tube 16 of the expandable reamer 10 may additionally include a guide pin 45 that is received within a slot 47 of the inner shaft 14 to guide the outer tube 16 as it moves relative to the inner shaft 14.

FIGS. 4 through 9 schematically illustrate an example method for removing diseased bone using the expandable reamer 10 described above and illustrated by FIGS. 1A, 1B, 2, 3A and 3B. The exemplary expandable reamer 10 provides a cutting blade 18 that can be incrementally controlled, thus controlling the size of a socket that is formed in bone. It should be understood that the method described herein and shown in FIGS. 4, 5, 6, 7, 8 and 9 may include a greater or fewer number of steps and that the steps could be performed in a different order within the scope of this disclosure.

Figure 4:
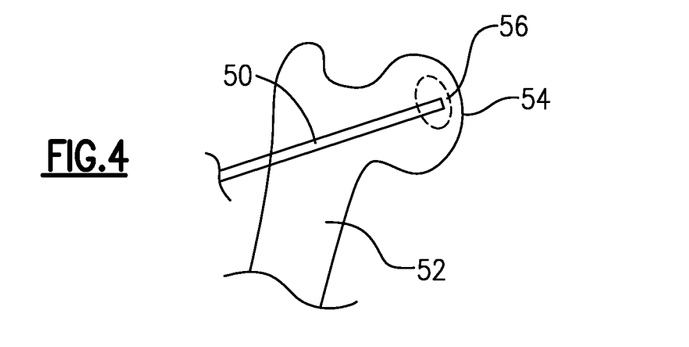
FIGS. 4, 5, 6, 7, 8 and 9 schematically illustrate an exemplary method of removing areas of diseased bone.

In one non-limiting embodiment, as illustrated by FIG. 4, the method begins by inserting a guide pin 50 into a bone 52.

In this embodiment, the bone 52 is a femur that includes a femoral head 54, although the method may be beneficially used elsewhere in a patient. A surgeon or other person of ordinary skill in the art would be able to select an appropriate positioning and/or placement of the guide pin 50 and could use fluoroscopic guidance and/or a targeting guide to achieve proper placement within the bone 52.

The guide pin 50 is inserted into diseased bone 56 (i.e., a lesion). In one embodiment, the guide pin 50 is positioned such that it does not pierce the endosteal surface of the femoral head 54. In other words, the method may be performed subchondrally.

Figure 5:
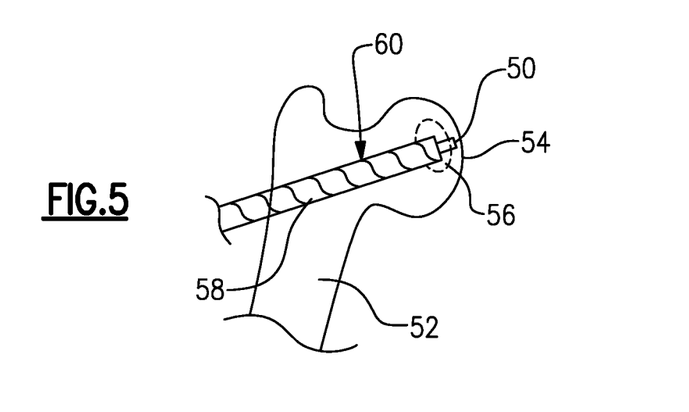

Once the guide pin 50 has been positioned, a cannulated drill bit 58 is placed over the guide pin 50 to ream a tunnel 60 into the bone 52, as shown in FIG. 5. The size of the guide pin 50 and the cannulated drill bit 58 may vary depending upon the size of the patient, among other criteria. Once the bone 52 has been reamed, the cannulated drill bit 58 and guide pin 50 may be removed.

Figure 6:
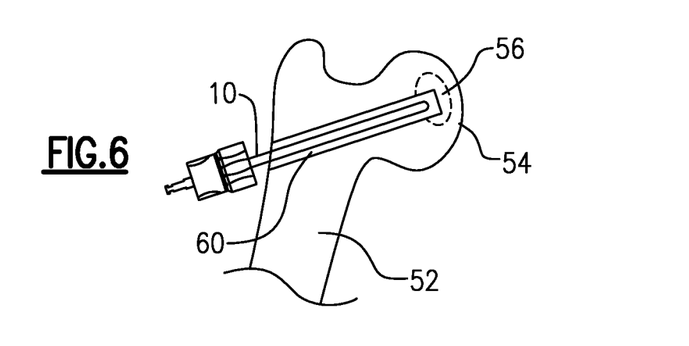

Next, as illustrated by FIG. 6, the expandable reamer 10 may be passed into the tunnel 60 and positioned within the bone 52 such that it extends into the diseased bone 56. During this step of positioning, the cutting blade 18 of the expandable reamer 10 is concealed inside of the outer tube 16 (see position P1 of FIGS. 1A and 3A). The tunnel 60 could alternatively be formed without using the guide pin 50.

Figure 7:
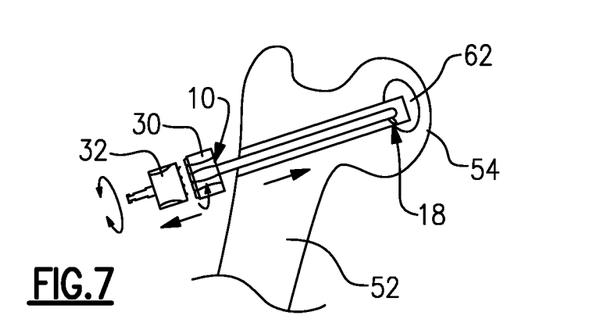

Referring now to FIG. 7, the cutting blade 18 of the expandable reamer 10 may next be incrementally to a cutting position. For example, the cutting blade 18 can be advanced by disengaging the clutch hub 32 from the threaded hub 30 and subsequently turning the threaded hub in the Z direction to effectuate axial movement of the outer tube 16, which is converted to rotational movement of the cutting blade 18 by the deflection pin 46 (see FIGS. 3A and 3B) to position the cutting blade 18 in the desired cutting position. The desired cutting position may vary depending on the amount of diseased bone 56.

Figure 8:
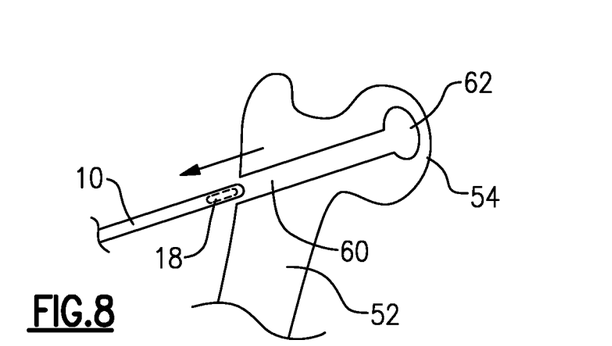

The entire expandable reamer 10 may then be rotated, such as with power equipment (not shown), to create a retrograded socket 62 in the bone 52 with the cutting blade 18, thereby removing the diseased bone 56. The cutting blade 18 may then be retracted (by turning the threaded hub 30 in an opposite direction) and the expandable reamer 10 removed from the bone 52 after the socket 62 has been adequately formed as shown in FIG. 8. The tunnel 60 and the socket 62 may be aspirated, such as with a combination of suction and irrigation, to remove any debrided tissue that may exist after reaming.

Figure 9:
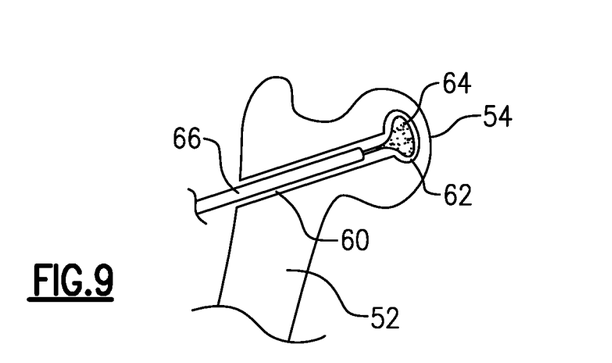

Finally, as shown in FIG. 9, the tunnel 60 and the socket 62 may be backfilled with a biologic 64. The biologic 64 could include a graft, a bone graft, calcium phosphate bone cement, or any other known biologic material. In one embodiment, the biologic 64 is injected with a needle 66 working from the socket 62 toward the tunnel 60. In another embodiment, the tunnel 60 and the socket 62 are completely filled with the biologic 64.

Figure 10A:
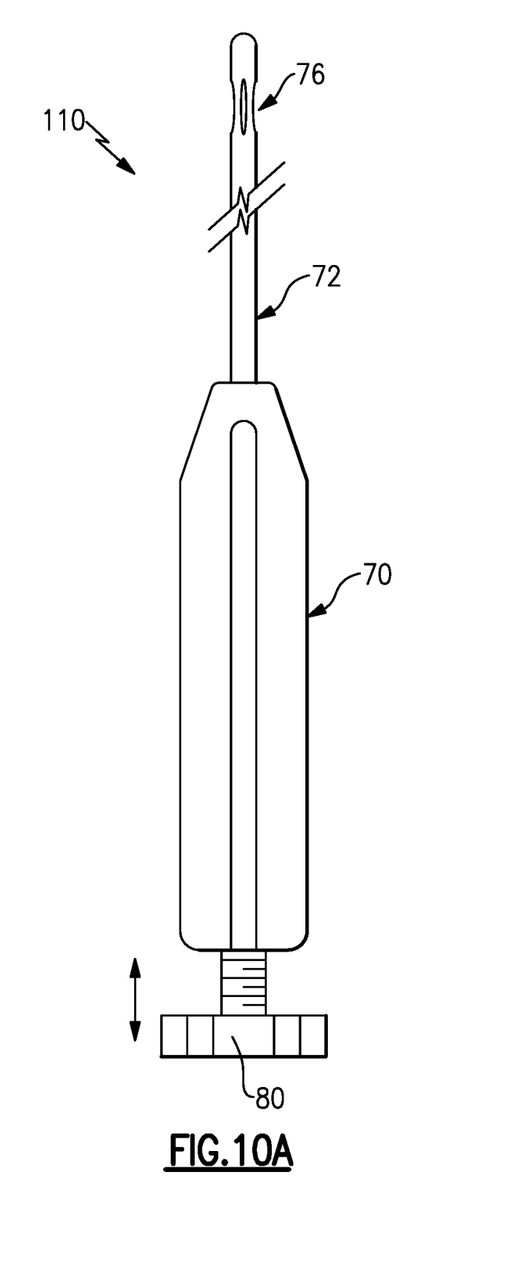
FIGS. 10A and 10B illustrate another exemplary expandable reamer.
Figure 10B:
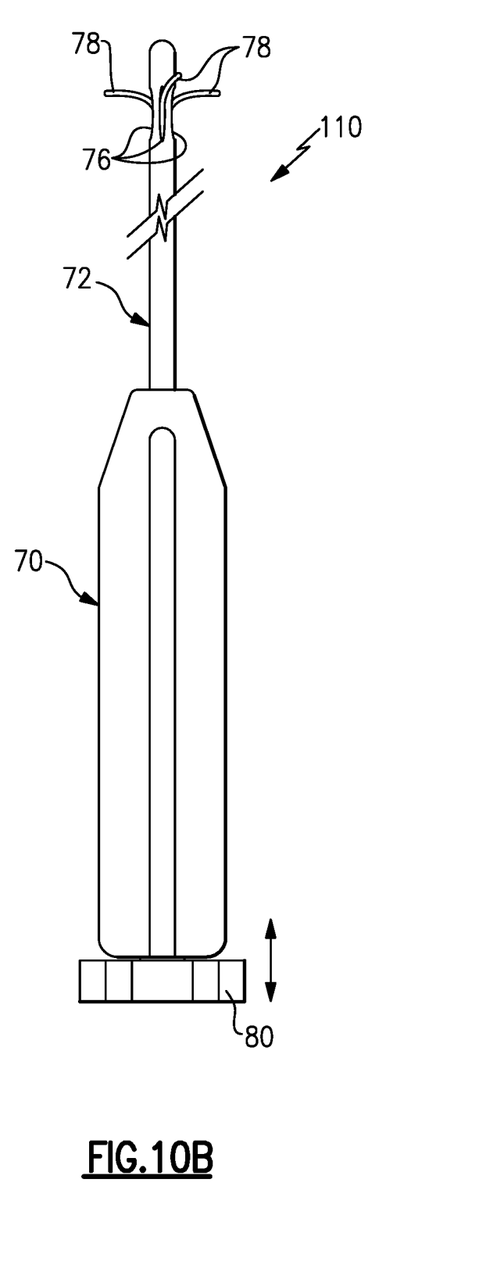

FIGS. 10A and 10B illustrate another exemplary expandable reamer 110. The expandable reamer 110 could be used in place of the expandable reamer 10 when performing the method shown in FIGS. 4 through 9, or some other similar method, for removing diseased bone. The expandable reamer 110 includes a handle 70 and a tube 72 that extends from the handle 70. In one embodiment, the handle 70 and the tube 72 are cannulated along their entire lengths. The tube 72 includes a plurality of windows 76. A plurality of cutting blades 78 are positioned inside of the tube 72 and may be incrementally advanced to protrude from the windows 76 in order to ream a socket in bone.

In one embodiment, the cutting blades 78 are expandable nitinol wires that have a shape memory. The handle 70 includes an actuator 80 that can be moved into the handle 70 (or vice versa) to position the cutting blades 78 radially outwardly from the windows 76 (i.e., a cutting position in which the cutting blades 78 are transverse to the tube 72). Movement of the actuator 80 in an opposite direction returns the cutting blades 78 to a straight position inside of the tube 72 (i.e., a closed position in which the cutting blades 78 are generally parallel to the tube 72). The actuator 80 can also be turned to adjust the shape of the cutting blades 78.

Figure 11A:
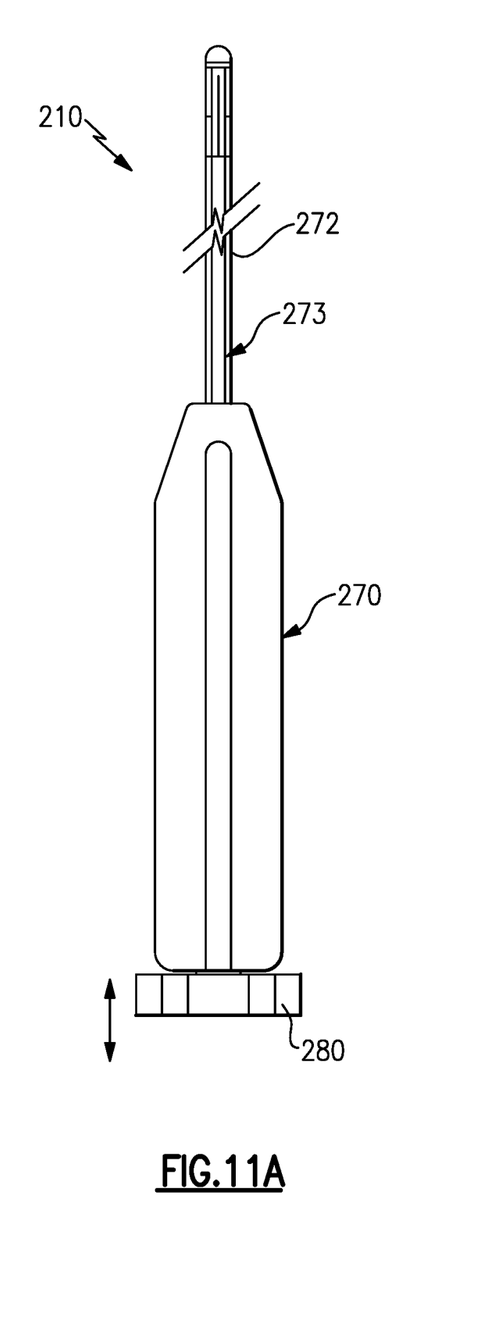
FIGS. 11A and 11B illustrate yet another exemplary expandable reamer.
Figure 11B:
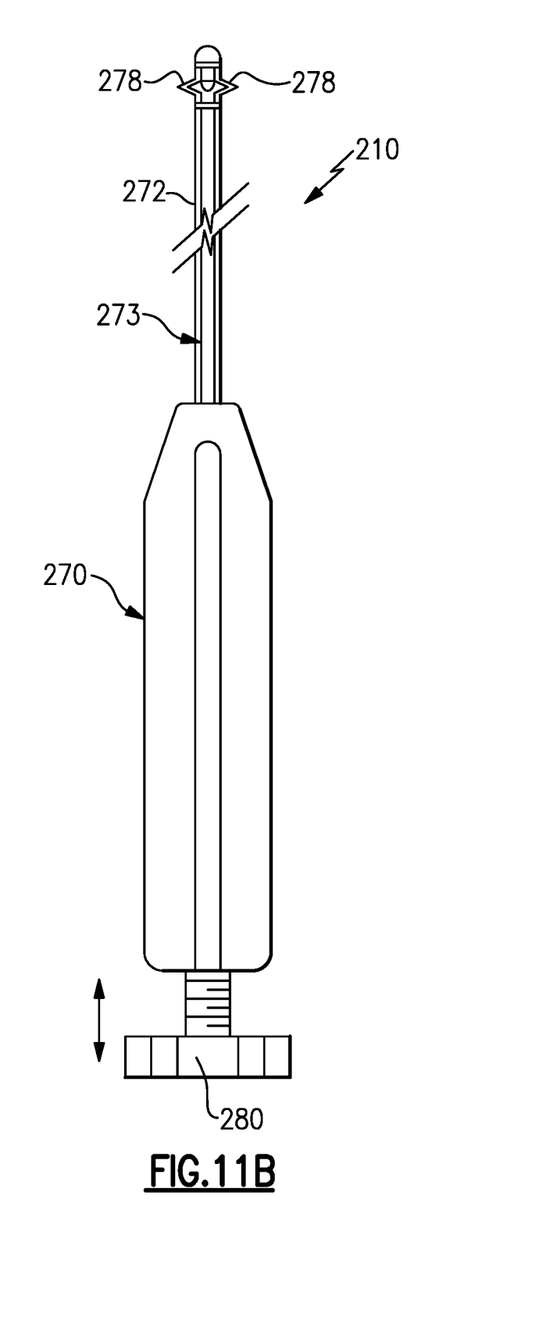

FIGS. 11A and 11B illustrate yet another exemplary expandable reamer 210 that can be used to remove diseased bone. In this embodiment, the expandable reamer 210 includes a handle 270, and an outer tube 272 and an inner shaft 273 that extend from the handle 270. The outer tube 272 generally surrounds the inner shaft 273. The handle 270 and the outer tube 272 may be cannulated along their entire lengths.

The inner shaft 273 can include a plurality of cutting blades 278 that may be incrementally advanced to protrude radially outward from the outer tube 272 in order to ream a socket in bone. In one embodiment, the cutting blades 278 are expandable nitinol wires that have a shape memory. The handle 270 includes an actuator 280 that can be moved away from the handle 270 (or vice versa) to move the outer tube 272, thereby positioning the cutting blades 278 radially outwardly to a cutting position. In one embodiment, movement of the outer tube 272 causes the cutting blades 278 to spring outwardly. Movement of the actuator 280 in an opposite direction returns the cutting blades 278 to a straight position inside of the outer tube 272 (i.e., a closed position).

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for removing a diseased bone comprising:
   reaming a tunnel into a bone;
   inserting an expandable reamer into the tunnel;
   rotating a clutch assembly of the expandable reamer,
     wherein rotating the clutch assembly moves a cutting blade of the expandable reamer between a first position in which the cutting blade is concealed inside a tube of the expandable reamer and a second position in which the cutting blade is exposed outside of the tube;
   rotating the expandable reamer while the cutting blade is in the second position to remove the diseased bone; and
   backfilling the tunnel with a biologic after removing the diseased bone, wherein rotating the clutch assembly causes a tapered edge of the cutting blade to be moved into contact with a deflection pin, thereby deflecting the cutting blade radially outward of the tube of the expandable reamer.

2. The method as recited in claim 1, wherein a rotational movement of a portion of the clutch assembly causes linear movement of the tube.

3. The method as recited in claim 2, wherein the deflection pin is configured to deflect the cutting blade to the second position as the cutting blade is moved into contact with the deflection pin during the linear movement.

4. The method as recited in claim 1, wherein rotating the clutch assembly includes:
disengaging a clutch hub from a threaded hub of the clutch assembly;
rotating the clutch hub relative to the threaded hub to effectuate an axial movement of the tube; and
converting the axial movement of the tube into rotational movement of the cutting blade via the deflection pin of the expandable reamer.

5. The method as recited in claim 1, wherein the biologic includes a graft, a bone graft, or a bone cement.

6. The method as recited in claim 1, wherein the bone is a femur that includes a femoral head, and further wherein the diseased bone includes a lesion located inside the femoral head.

7. The method as recited in claim 1, wherein the cutting blade is hinged to a shaft of the expandable reamer by a pin such that the cutting blade rotates about an axis that extends through the pin as the clutch assembly is rotated.

8. A method for removing a diseased bone comprising:
positioning a surgical device relative to the diseased bone, the surgical device including at least one cutting blade that is concealed inside the surgical device during the step of positioning; and
incrementally advancing the at least one cutting blade to position the at least one cutting blade into a cutting position relative to the diseased bone,
wherein incrementally advancing the at least one cutting blade includes rotating a clutch assembly of the surgical device,
wherein rotating the clutch assembly includes rotating a clutch hub relative to a threaded hub of the clutch assembly to effectuate an axial movement of a tube or a shaft of the surgical device,
wherein the axial movement is converted into a rotational movement of the at least one cutting blade via a deflection pin of the surgical device,
wherein the deflection pin deflects the at least one cutting blade radially outward of the tube as a tapered edge of the at least one cutting blade is moved into contact with the deflection pin in response to rotating the clutch assembly.

9. The method as recited in claim 8, comprising:
rotating the surgical device to remove the diseased bone.

10. The method as recited in claim 8, comprising:
reaming a tunnel into a bone that includes the diseased bone prior to positioning the surgical device.

11. The method as recited in claim 10, comprising:
backfilling the tunnel with a biologic after incrementally advancing the at least one cutting blade.

12. The method as recited in claim 11, wherein backfilling the tunnel includes injecting the biologic with a needle.

13. The method as recited in claim 11, wherein the biologic includes a graft, a bone graft, or a bone cement.

14. The method as recited in claim 8, wherein the step of incrementally advancing the at least one cutting blade includes axially moving a tube or shaft of the surgical device to rotationally move the at least one cutting blade to the cutting position.

15. A method for removing a diseased bone comprising:
reaming a tunnel into a femoral head of a femur,
wherein the diseased bone includes a lesion located inside the femoral head;
inserting an expandable reamer into the tunnel;
rotating a clutch assembly of the expandable reamer,
wherein rotating the clutch assembly moves a cutting blade of the expandable reamer between a first position in which the cutting blade is concealed inside a tube of the expandable reamer and a second position in which the cutting blade is exposed outside of the tube,
wherein rotating the clutch assembly causes a tapered edge of the cutting blade to be moved into contact with a deflection pin, thereby deflecting the cutting blade radially outward of the tube;
rotating the expandable reamer while the cutting blade is in the second position to remove the lesion; and
backfilling the tunnel with a biologic after removing the lesion,
wherein the method treats avascular necrosis (AVN) of a hip.

* * * * *